United States Patent [19]

Kirkland et al.

[11] Patent Number: 5,869,724
[45] Date of Patent: Feb. 9, 1999

[54] ASYMMETRIC BIDENTATE SILANES

[75] Inventors: Joseph J. Kirkland, Wilmington; John B. Adams, Jr., Hockessin, both of Del.

[73] Assignee: Hewlett-Packard Company, Palo Alto, Calif.

[21] Appl. No.: 879,541

[22] Filed: Jun. 20, 1997

[51] Int. Cl.$^6$ .................................................. C07F 7/10
[52] U.S. Cl. .................. 556/410; 556/431; 556/434; 502/407; 210/198.2; 210/656; 428/403; 428/404; 428/405; 428/406; 428/407; 428/447; 55/67
[58] Field of Search .................. 556/410, 431, 556/434; 502/407; 210/198.2, 656; 428/403, 404, 405, 406, 407, 447; 55/67

[56] References Cited

U.S. PATENT DOCUMENTS

| | | | |
|---|---|---|---|
| 2,561,429 | 7/1951 | Sveda | 556/434 |
| 3,172,874 | 3/1965 | Klebe | 556/410 X |
| 3,336,352 | 8/1967 | Omientanski | 556/410 |
| 3,431,222 | 3/1969 | Fink | 556/410 X |
| 3,497,539 | 2/1970 | Goossens | 556/410 |
| 3,505,381 | 4/1970 | Kotzsch et al. | 556/410 |
| 3,505,785 | 4/1970 | Kirkland . | |
| 3,658,865 | 4/1972 | Bakassian et al. | 556/431 |
| 3,674,739 | 7/1972 | Goossens | 556/410 X |
| 3,722,181 | 3/1973 | Kirkland et al. . | |
| 3,782,075 | 1/1974 | Kirkland . | |
| 3,795,313 | 3/1974 | Kirkland et al. . | |
| 3,892,678 | 7/1975 | Halasz et al. | 556/410 X |
| 3,979,546 | 9/1976 | Lewis . | |
| 4,010,042 | 3/1977 | Bover . | |
| 4,010,242 | 3/1977 | Iler et al. . | |
| 4,131,542 | 12/1978 | Bergna et al. . | |
| 4,504,549 | 3/1985 | Pines et al. . | |
| 4,600,646 | 7/1986 | Stout . | |
| 4,666,717 | 5/1987 | Smith et al. . | |
| 4,699,717 | 10/1987 | Riesner et al. . | |
| 4,745,572 | 5/1988 | Glajch et al. . | |
| 4,874,518 | 10/1989 | Kirkland et al. . | |
| 5,108,595 | 4/1992 | Kirkland et al. . | |
| 5,250,648 | 10/1993 | Huggins | 556/410 U X |

FOREIGN PATENT DOCUMENTS 0 129 074  12/1984  European Pat. Off. .

OTHER PUBLICATIONS

Jones et al., Characterization and Evaluation of Cyanopropyl Polysiloxane Stationary Phases for Gas Chromatograph, 1984, vol. 298, pp. 389–397, Journal of Chromatography.

Lork et al., Role of the Functional Group in n–Octyldimethylsilances in the Synthesis of $C_8$ Reversed–Phase Silica Packings for High Performance Liquid Chromatography, (1986), vol. 352, pp. 199–211, Journal of Chromatography.

Boksanyi et al., Reaction of n–Alkylkimethylsilanols and n–Oxaalkyldimethylsilanols with the Hydrated Surface of Silicon Dioxide —The Question of the Limiting Surface Concentration, (1976), vol. 6, pp. 95–137, Advances in Colloid and Interface Science.

Sindorf et al., Solid–State NMR Studies of the Reactions of Silica Surfaces with Polyfunctional Chloromethylsilanes and Ethoxymethylsilanes, 1983, vol. 105, pp. 3767–3776, J. Am. Chem. Soc.

Welsch et al., Characterization of a New Dehydroxylated Reversed–Phase Material, 1983, vol. 267 pp. 39–48, Journal of Chromatography.

1985, vol. 103, p. 668, 71494v, Chemical Abstracts.

R.K. Iler "The Chemistry of Silica," pp. 97–98, John Wiley, NY, NY (1979).

Kirkland et al., Synthesis and Characterization of Highly Stable Bonded Phases for High–Performance Liquid Chromatography Column Packings, 1988, vol. 61, pp. 2–11, J. Am. Chem. Soc.

Kirkland et al., Stability of Silica–Based, Endcapped Columns with pH 7 and 11 Mobile Phases for Reversed–Phase High–Performance Liquid Chromatography, 1997, vol. A762, pp. 97–112, Journal of Chromatography.

Kirkland et al., High pH Mobile Phase Effects on Silica–Based Reversed–Phase High–Performance Liquid Chromatographic Columns, 1995, vol. A691, pp. 3–19, Journal of Chromatography.

Claessens et al., Effect of Buffers on Silica–Based Column Stability in Reversed–Phase High–Performance Liquid Chromatography, 1996, vol. A728, pp. 259–270, Journal of Chromatography.

Smith et al., The Efficient Analysis of Neutral and Highly Polar Pharmaceutical Compounds Using Reversed–Phase and Ion–Exchange Electrochromatography, 1995, pp. 197–203, Chromatographia vol. 41, No. 3/4.

L.R. Snyder and J.J. Kirkland, "An Introduction to Modern Liquid Chromatograph," Chapter 7, John Wiley, NY, NY (1979).

*Primary Examiner*—Paul F. Shaver
*Attorney, Agent, or Firm*—Richard F. Schuette

[57] ABSTRACT

The present invention provides asymmetric bidentate silane reagents from modifying the surface of liquid chromatography supports, the supports and methods of making and using the same. When bonded to the surface of a support material, the resulting modified support material provides improved properties, such as better separations and more stable support materials, especially when used in liquid chromatography. These bidentate silanes have the general structure: $R_1SiMe(NMe_2)$—$(CH_2)_n$—$SiMeR_2(NMe_2)$. $R_1$ is an alkyl group having from 1 to 30 carbon atoms, and $R_2$ is an alkyl group having from 8 to 18 carbon atoms. $R_1$ is a different alkyl group than $R_2$. Me is a methyl group, and n has a value 2 or 3. In certain embodiments, $R_2$ includes at least one functional group. When reacted with a silica surface, the resulting modified surface has a structure: PSiO—[$R_1SiMe$—$(CH_2)_n$—$SiMeR$]—OSiP. PSiO is a surface reacted silica.

12 Claims, 4 Drawing Sheets

ASYMMETRIC BIDENTATE SILANES

BACKGROUND OF THE INVENTION

1. Field of the Invention

The present invention relates generally to asymmetric bidentate silane reagents for modifying the surface of liquid chromatography supports, these surface modified supports and methods of making and using the same.

2. Discussion of Related Art

Liquid chromatography is an analytical method used to separate one or more species, such as ions or solutes, present in a carrier phase (i.e., solution) from the remaining species in the carrier phase. The carrier phase is typically passed through an open column packed with a granular material, commonly referred to as the support material. The most common support materials are silica-based.

The rate at which a particular solute passes through a chromatographic column depends upon the affinity of the solute for the support material, with solutes having a higher affinity for the support material passing through the column at slower rates. In certain cases, the affinity of a particular solute for the support material may be so high that essentially none of it passes through the column, resulting in substantially complete separation of that solute from the remaining species present within the carrier phase.

In large part, the affinity a solute has for a support material depends upon the functional groups present at the surface of the particles of the support material. Therefore, in many circumstances, it is desirable to bond modifying reagents containing certain functional groups to the surface of these particles to manipulate the rate at which different species pass through the column. For example, to separate an anionic species present in a carrier phase from a cationic species present in the carrier phase, a modifying reagent having cationic functional groups may be bonded to the surface of the particles of support material.

In addition to the functional groups contained within a surface modifying reagent, the strength of the bond between the reagent and the surface of a support material (i.e., stability of the modifying reagent) should be considered when choosing the reagent. If the bond between the modifying reagent and the support material surface is not strong enough, the modifying reagent can be released from the substrate during a liquid chromatography experiment. This can contaminate the separation product and/or reduce the efficiency of separation. Moreover, the ability of the modified support material to be re-used can be limited. Generally, a surface modifying reagent that bonds to the surface of a support material through two reagent atoms is more stable than a similar surface modifying reagent that only bonds to the surface through one reagent atom.

Still another factor to be considered when selecting a surface modifying reagent is the molecular structure that the reagent exhibits after it is bound to the surface of the support material. For example, the inherent variation of certain chemical and physical properties of polymers can result in problems with predicting the affinity of a given species for support materials having polymeric surface modifying reagents bonded thereto. Moreover, polymeric surface modifying reagents can cause problems with mass transport of a carrier phase through a liquid chromatography column, decreasing the efficiency of separation.

Silanes are the most commonly used surface modifying reagents in liquid chromatography. For example, "An Introduction to Modern Liquid Chromatography," Chapter 7, John Wiley & Sons, New York, New York 1979; J. Chromatogr. 352, 199 (1986); J. Chromatogr., 267, 39 (1983); and Advances in Colloid and Interface Science, 6, 95 (1976) each disclose various silicon-containing surface modifying reagents. However, these reagents bond to the surface of support materials through only one silicon atom, reducing the stability of these substrate-reagent bonds.

U.S. Pat. Nos. 3,722,181 and 3,795,313; EP Patent Application 129,074; J. Chromatogr. 298, 389 (1984); and Angew. Cheme. Int. Ed. Engl. 25, 236 (1986) each disclose polymeric silicon-containing surface modifying reagents, but, according to U.S. Pat. No. 4,746,572, discussed below, the use of these reagents has resulted in problems with mass transport of carrier phases through columns. In addition, these columns can demonstrate a lack of predictability with respect to the affinity of certain species for the support materials, according to U.S. Pat. No. 4,746,572.

U.S. Pat. No. 4,746,572 discloses bidentate silanes for use as surface modifying reagents in liquid chromatography. This reference emphasizes the use of symmetric bidentate silanes. However, as demonstrated in examples disclosed below, support materials having symmetric bidentate silanes bound thereto can demonstrate nonoptimal performance in some liquid chromatography separations.

From the foregoing discussion, it is clear that, despite the extensive efforts made in the art to provide improved surface modifying reagents for use in liquid chromatography, there remains a need to provide such reagents that exhibit improved stability under experimental conditions and predictability with respect to affinity to species in carrier phases. It would be advantageous for such reagents to be readily synthesized and easily bound to the surface of support materials.

SUMMARY OF THE INVENTION

In its broadest aspects, the present invention relates to asymmetric bidentate silanes that can be bonded to the surface of support materials to provide modified support materials that provide improved separations and higher predictability.

In one illustrative embodiment, the present invention provides a support composition having a structure: PSiO—[$R_1$SiMe—$(CH_2)_n$—SiMe$R_2$]—OSiP. $R_1$ is an alkyl group having from 1 to 30 carbon atoms, and $R_2$ is an alkyl group having from 8 to 18 carbon atoms. $R_1$ is a different alkyl group than $R_2$. Me is a methyl group, and n has a value of 2 or 3. PSiO is a surface-reacted silica.

In another illustrative embodiment, the present invention provides a bidentate silane having a structure: $R_1$SiMe$(NMe_2)$—$(CH_2)_n$—SiMe$R_2(NMe_2)$. $R_1$ is an alkyl group having from 1 to 30 carbon atoms, and $R_2$ is an alkyl group having from 8 to 18 carbon atoms. $R_1$ is a different alkyl group than $R_2$ Me is a methyl group, and n has a value of 2 or 3.

In a further illustrative embodiment, the present invention provides a bidentate silane having a structure: $R_1$SiMeCl—$(CH_2)_n$—SiMeCl$R_2$. $R_1$ is an alkyl group having from 1 to 30 carbon atoms and $R_2$ is an alkyl group having from 8 to 18 carbon atoms. Me is a methyl group, and n has a value of 2 or 3.

BRIEF DESCRIPTION OF THE DRAWINGS

These and other advantages of the present invention will be more clearly understood when taken in conjunction with the following detailed description and figures, in which.

DETAILED DESCRIPTION OF THE INVENTION

Figure 1:
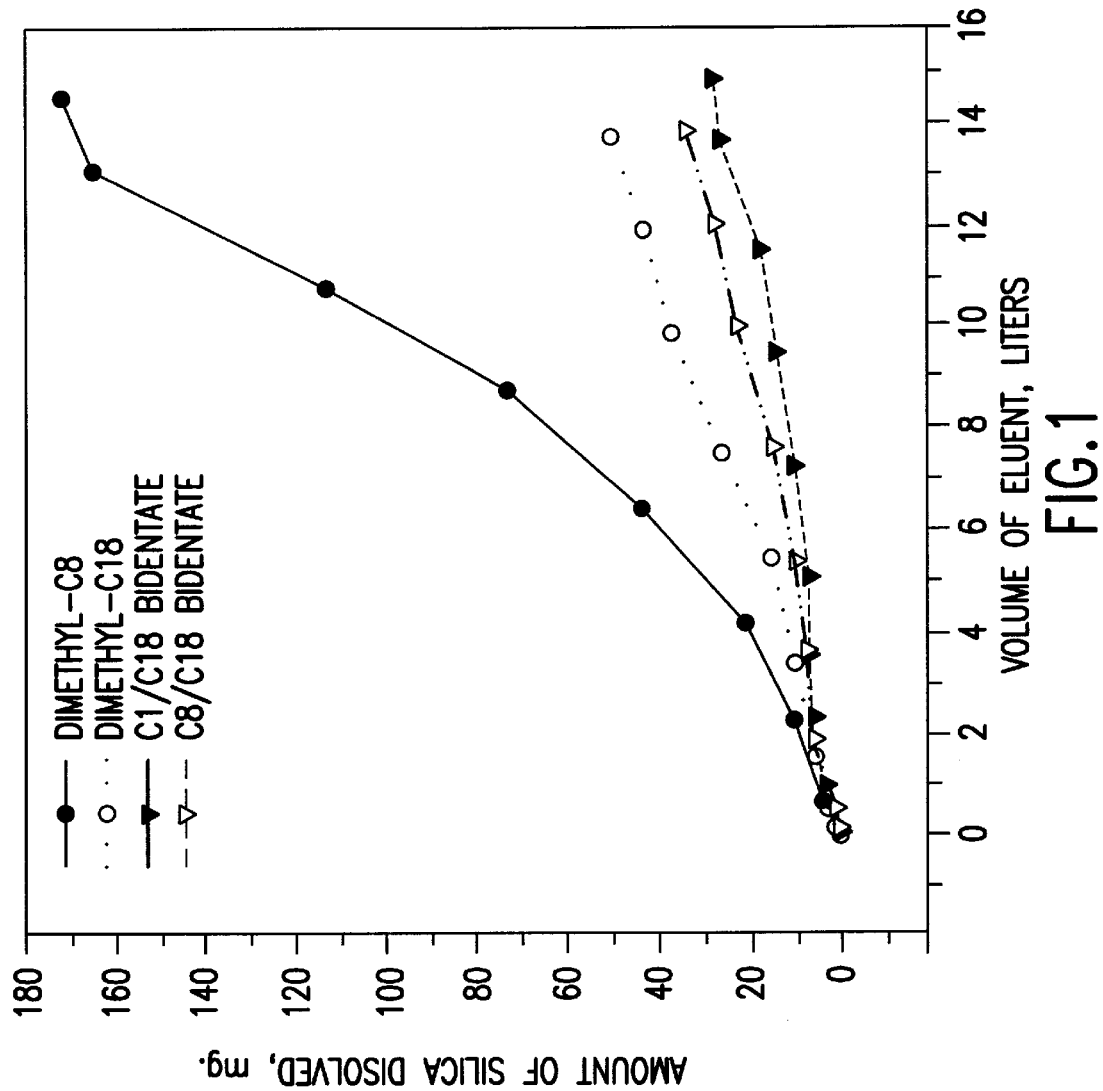
FIG. 1 is a graph comparing the dissolution of modified support materials according to two embodiments of the present invention with that of support materials according to the related art.

The present invention relates to asymmetric bidentate silanes which can be used as surface modifying species for chromatography support materials. It has been found that the resulting surface modified support materials provide more efficient separations. The asymmetric bidentate silanes can be used in a variety of chromatography solid phase supports. Liquid column chromatography, capillary electrophoresis, capillary electrochromatography, thin layer chromatography, affinity separations and the like can benefit from the use of the asymmetric bidentate silanes of the present invention. It has been demonstrated that the asymmetric bidentate silanes also exhibit a reduced rate of support material dissolution during liquid chromatography procedures.

The term "asymmetric" bidentate silane as used herein refers to a bidentate silane reagent having a molecular formula:

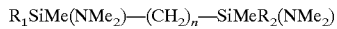

$R_1SiMe(NMe_2)$—$(CH_2)_n$—$SiMeR_2(NMe_2)$ wherein n has a value of 2 or 3, Me is a methyl group, $R_1$ is a $C_1$ to $C_{30}$ alkyl group, and $R_2$ is a $C_8$ to $C_{18}$ alkyl group. $R_1$ and $R_2$ are not the same alkyl group. In certain embodiments, $R_2$ may be a $C_8$ to $C_{18}$ alkyl group that is substituted with —$(CH_2)_3$—$N^+Cl^-$, —$(CH_2)_2$—$C_6H_4$—$SO_3H$, —$(CH_2)_3$—$C_6H_4$—$SO_3H$, —$(CH_2)_3$—$O$—$CH_2$—$CHOH$—$CH_2OH$, —$(CH_2)_3$—$NH_2$, or —$(CH_2)_3$—$CN$.

An illustrative and nonlimiting list of examples of asymmetric bidentate silanes (dimethylamino groups bonded to each silicon atom of each silane not shown) according to the present invention includes: Me($C_8H_{17}$)—Si—$(CH_2)_2$—Si—Me($C_{18}H_{37}$), Me($C_4H_9$)—Si—$(CH_2)_2$—Si—Me($C_{18}H_{37}$), Me$_2$—Si—$(CH_2)_2$—Si—Me($C_{18}H_{37}$), Me($C_{14}H_{29}$)—Si—$(CH_2)_2$—Si—Me($C_{18}H_{37}$), Me($C_{30}H_{61}$)—Si—$(CH_2)_2$—Si—Me($C_{18}H_{37}$), Me($C_{30}H_{61}$)—Si—$(CH_2)_2$—Si—Me($C_{14}H_{29}$), Me($C_8H_{17}$)—Si—$(CH_2)_2$—Si—Me($C_{14}H_{29}$), Me($C_8H_{17}$)—Si—$(CH_2)_3$—Si—Me($C_{18}H_{37}$), Me($C_4H_9$)—Si($CH_2$)$_3$—Si—Me($C_{18}H_{37}$), Me$_2$—Si—$(CH_2)_3$—Si—Me($C_{18}H_{37}$), Me($C_{14}H_{29}$)—Si—$(CH_2)_3$—Si—$(CH_2)_3$—Si—Me($C_{18}H_{37}$), Me($C_{30}H_{61}$)—Si—$(CH_2)_3$—Si—Me($C_{18}H_{37}$), Me($C_{30}H_{61}$)—Si—$(CH_2)_3$—Si—Me($C_{14}H_{29}$) and Me($C_8H_{17}$)—Si—$(CH_2)_3$—Si—Me($C_{14}H_{29}$).

Certain unexpected advantages associated with the asymmetric bidentate silanes of the present invention now will be described. When optimizing the ability of a bidentate silane surface modifying reagent to improve the performance of a support material formed from silica, it is often advantageous to be able to control the affinity of a particular species in the carrier phase for the support material. As discussed in U.S. Pat. No. 4,746,572, referenced above, bidentate silane surface modifying reagents can exhibit improved performance in liquid chromatography procedures because each surface-modifying molecule includes two points of covalent attachments to the surface of the chromatography support material.

Without wishing to be bound by any theories, it is believed that asymmetric bidentate silanes exhibit improved performance over symmetric bidentate silanes because asymmetric bidentate silanes allow control over the spacing between specific hydrocarbon groups (or functional groups) ($R_1$ and $R_2$, above) of interest at the surface of a support material. This results in a modified surface structure having the desired affinity for a particular species in the carrier phase, with desired spacing between functional groups providing the desired affinity. That is, the present invention facilitates immobilization of a particular hydrocarbon group at a chromatography support surface, via a bidentate silane, with the particular hydrocarbon group being essentially evenly distributed across the surface at essentially any amount of surface coverage. For example, where it is desired to immobilize a $C_{18}$ alkyl group as a surface-modifying species at a chromatography support surface, but it is desirable to space the $C_{18}$ alkyl group from each other to avoid aggregation or other interaction between the chains (so as to allow the carrier phase to interact to a maximum extent with the 1 8-carbon chains) an asymmetric bidentate silane in which $R_1$ is a methyl group and $R_2$ is a $C_{18}$ alkyl group can be applied to the support surface in a desired concentration. The bidentate silane will covalently attach, under conditions described herein, to the support surface and, depending upon the amount of bidentate silane exposed to the surface (concentration of bidentate silane in a delivering fluid medium) the concentration of $C_{18}$ alkyl group bonded to the substrate surface can be controlled, and the $C_{18}$ alkyl groups will be spaced from each other in a manner identical to the spacing of the bidentate silanes from each other. This is in contrast to a symmetric bidentate silane desirably used to impart 18-carbon chain functionality to a support surface. In that instance, each bidentate silane will include at least two $C_{18}$ alkyl groups, thus the spacing between $C_{18}$ alkyl groups will be dictated by the interatomic spacing of the bidentate silane reagent regardless of the spacing between bidentate silane molecules at the surface. This can be extremely beneficial when, as mentioned above, it is desirable to maximize chromatography mobile phase interaction with modified support surface functionality. This improvement of the present invention is believed to be enhanced for asymmetric silanes in which $R_1$ is a methyl group. Support materials modified with these asymmetric silanes have good hydrophobicity without aggregation of the silanes at the surface of the support structure.

The asymmetric bidentate silanes of the present invention can be reacted with silanol groups (Si—OH) at the surface of a silica support (packing material) to provide a support composition or surface complex or derivatives (modified support surface) having a molecular formula:

PSiO-[$R_1$SiMe—$(CH_2)_n$—SiMeR$_2$]—OSiP wherein PSiO is a surface-reacted silica (i.e., silica that has undergone reaction with an asymmetric bidentate silane).

The word "bond" herein denotes a chemical bond, such as a covalent bond. Thus, for example, the interaction between a silicon atom and an oxygen atom located at a silica surface may result in a covalent bond between the silicon atom and the oxygen atom.

While silica is the preferred support material, other materials appropriate for use in the present invention are known to those skilled in the art and are intended to be within the scope of the present invention. For example, in certain embodiments, a hydroxylated organic polymer or plastic can be used.

In certain embodiments, a silica substrate may have a relatively small number of silanol groups present at its surface. For such embodiments, it may be desirable to hydrolyze the surface of the support material to increase the number of hydroxyl groups present at the surface of the support material. Such hydrolysis methods are known to those skilled in the art and are intended to be within the scope of the present invention. For example, surface hydrolysis of silica may be accomplished by reacting the support material with water in the presence of HF or at least one basic activator selected from the group consisting of quaternary ammonium hydroxides, ammonium hydroxide and organic amines at a temperature of from about 25° C. to about 100° C. for a period of time sufficient to generate the desired surface concentration of silanol groups (Si-OH).

The concentration of silanol groups on a silica surface can be determined in several ways including infrared spectroscopy, solid-state magic angle spinning nuclear magnetic resonance, proton spin counting space NMR, and/or thermogravimetric analysis, the latter generally being preferred because of its simplicity and precision. It is noted in this connection that excessive rehydroxylation of a silica surface to greater than about $8\mu$ mol/m$^2$ of silanol groups will result in silanol groups that are "buried" beneath the silica surface. These groups are detected by TGA, but generally are not available for chromatographic interactions or for reactions with silanizing agents to form bonded-phase packings.

It has been found that activators which promote rehydroxylation to the desired total concentration of silanol groups of from about 6 to about $16\mu$ mol/m$^2$ are HF and basic activators selected from the group consisting of quaternary ammonium hydroxides, ammonium hydroxide and organic amines. Preferably, the basic activator is selected from the group consisting of tetra alkylammonium hydroxide, ammonium hydroxides, primary organic amines and secondary organic amines. The relative rate of dissolution of silica by a basic activator can be controlled by maintaining pH in the weakly-basic range. Most primary and secondary organic bases rapidly dissolve silica above a pH of about 10.5. The rate is much slower below this pH value. A basic activator that provides a buffered pH of about 10.5 in dilute solution has desirable properties, especially when hydroxylation is carried out in a temperature range of from about 25° C. to about 50° C. At these temperatures, the solubility and the rate of transfer of silica is much lower than at higher temperatures, such as 100° C. Preferably, a basic activator is added in an amount sufficient to generate a pH of from about 9 to about 10.5.

For basic activators, the overall rate of attack on the silica surface generally decreases from methyl to ethyl to propyl. For example, normal ethyl-, propyl-, and butylamine, secondary ethyl-propyl- and butylamine are effective activators. Monomethyl- and dimethyl- are dimethylamine can be utilized, if care is exercised. Steric effects appear to have a not a noticeable influence on the dissolution rate of the silica gel lattice as disclosed by J. Chromatogr., Volume 149, 199 (1978). Methyl amines can be less practical because of their strong tendency to attack silica. Thus, methyl amines are more difficult to control in generating the desired concentration of silanol groups. It has been found that the rate of attack of a base on silica is dependent on the strength (pK$_B$ value), concentration, and geometry of a selected basic activator.

Although tetraalkylammonium hydroxides show strong aggressiveness for dissolving silica, these compounds are preferred basic activators for rehydroxylation. This is the case even though tetramethylammonium, tetrapropylammonium and tetrabutylammonium hydroxide show equal or an even greater tendency than alkali hydroxides to attack the silica surface. Tetraalkylammonium hydroxides are effective activators because at a pH of from about 9 to about 10.5, very little of the free base remains in solution. It is believed that most of the base is absorbed as a monolayer on the silica surface, making the silica somewhat hydrophobic. Hydroxyl ions remaining in solute catalyze the breaking of siloxane groups, while the monolayer of activator on the silica surface retards dissolution and deposition of silica. Therefore, the process can be conveniently interrupted before the degree of hydroxylation passes beyond the desired range.

Ammonium hydroxide is also a preferred basic activator. Dilute ammonium hydroxide a pH 10 reacted with silica for 18 hours and 25° C. is a preferred method for rehydroxylating a silica surface to the desired concentration if silanol groups. Hydrolysis of a 440 m$^2$/g silica by this procedure changed the surface area by only about 25%, and the pore volume of the silica remained essentially unchanged.

Most preferably, the basic activator is at least one primary amine selected from the group consisting of ethylenediamine, n-propylamine and n-butylamine. These amines can generate a pH of from about 9 to about 10.5. A pH in this range accelerates rehydroxylation of the silica surface, without significant change in the surface area and pore diameter of the silica structure as can occur with strong organic bases such as quaternary ammonium hydroxides. When the latter are used as activators, their concentration should be low and the initial pH should be not exceed about 10. Secondary amines such as diethyl-, dipropyl-, and dibutylamine are also suitable activators but rehydroxylation reactions are generally slower. Tertiary amines are less preferred activators.

Alkali- or alkaline-earth hydroxides such as NaOH, KOH and Ca(OH)$_2$ are difficult to control in the rehydroxylation process. Use of these agents can result in significant undesirable changes in the pore structure and surface area of the starting silica. In addition, use of these agents results in an undesired contamination of the starting silica with the cation from the hydroxide. This contamination causes deleterious effects with the silica support in subsequent chromatographic uses.

Acidic solutions of ionic fluorides are also suitable activators. Suitable sources of HF are HF, NH$_4$F and other ionic fluorides not containing a metal or metalloid cation which could deleteriously contaminate the highly purified silica. These activators can be added to an aqueous solution containing thermally dehydroxylated microspheres according to the following procedure. The aqueous solution is adjusted to a pH of about two to about four with a mineral acid such as hydrofluoric, hydrochloric or sulfuric acid. A suitable source of free HF is added to the solution in a concentration that acts as a catalytic agent for the dissolution of the silica surface. The preferred concentration of HF is a function of the surface area of the silica. Preferably, silica microspheres are rehydroxylated in the presence of free HF in a concentration of from about 50 to about 200 to about 400 ppm is suitable to activate the rehydroxylation of a 300–400m²/g silica. It is believed that fluoride, introduced as HF or an ionic slat thereof at a pH from about 2 to about 4, reacts with a small amount of dissolved silica to from $SiF_6^{-2}$. The $SiF_6^{-2}$ remains in equilibrium with a low concentration of HF. The fluoride ion at low pH functions as an activator to increase the rate of silica hydroxylation.

In addition to having atoms capable of reacting with an asymmetric bidentate silane located at its surface, a support material should provide the shape, rigidity, porosity and other physical characteristics desired for a given application. Preferably, a substrate is formed from a solid material, however, liquids and gases are also intended to be within the scope of the present invention. Generally, a support material can be in the form of various shapes as spheres, irregular shaped articles, rods, plates, films sheets, fibers, massive irregularly shaped objects and the like. Moreover, a support material can be porous or nonporous. In embodiments in which a support material is porous, where the pores are larger than an asymmetric bidentate silane reacted with the support material, the interior surfaces of the pores can have the asymmetric bidentate silane bonded thereto. For such embodiments in which the pores are smaller than the silane, the silane typically bonds only to the outside surface of the support material. Moreover, in many applications, it is advantageous to use a support material that is stable to temperatures of at least 200° C. The choice of support material depends upon the ultimate application, and one skilled in the art will readily recognize which properties a support material should have for a given use.

The support materials of the present invention are generally useful whenever highly stable surface modification of a liquid chromatography support material is desirable, and the functional groups introduced by the asymmetric bidentate silanes of the present invention can be used in many ways. In particularly advantageous embodiments, the modified support materials are used as a point of attachment for substances of biological or synthetic organic interest, such as, for example, peptides, proteins and oligonucleotides. In these embodiments, synthesis of a desired biopolymer can be achieved by repetitive addition of individual monomers to the bidentate silane bonded to the substrate. The final biopolymer typically comprises 5 to 50 monomer units and typically is cleaved from the silane before use. The success of these syntheses depends upon many factors, one of which is the chemical stability of the substrate-to-silane bond. Known support materials often exhibit relatively short lifetime, which can cause problems with the reproducibility of results, usually leading to frequent replacement of the support material. In contrast, the relatively long lifetimes of the modified support materials of the present invention can be especially effective as stable, efficient media in the synthesis of biological or synthetic organic substances. In some embodiments, the modified support materials of the present invention can be used in conjunction with automated peptide, protein, and nucleotide synthesizer instruments.

In alternate embodiments, the support materials of the present invention are useful in applications in which it is advantageous to have a stable bond between a surface modifying species and a support material, such as in polypeptide sequencing applications. In these embodiments, the polypeptide to be sequenced is typically adsorbed to a filter disk coated with a non-bonded material such as Polybrene®, a polymeric quaternary amine. The polypeptide is then subjected to repetitive chemical degradation. A major disadvantage of this approach has been that the yields of the repetitive process are poor, at least in part due to loss of the non-bonded coating. However, substitution of the highly stable, modified support materials of the present invention can overcome these difficulties.

Reaction of the asymmetric bidentate silanes with a silica support should occur under conditions where the amount of water in the reaction mixture is sufficient to react with enough bidentate silane to deliteriously effect the synthesis process (dry conditions). Preferably, the reaction is carried out using a solvent that does not chemically react with the reagents used during synthesis of the support composition. Such inert solvents include, for example, toluene, xylene and cymene. In certain embodiments, the solvent may be heated.

The chemistry of silanes with various surfaces is well-studied. A general discussion of the reaction of silanes with the surface of siliceous chromatographic support materials is provided in "An Introduction to Modern Liquid Chromatography," L. R. Snyder and J. J. Kirkland, Chapter 7, John Wiley and Sons, N.Y., N.Y. (1979). Additional details on the reaction of silanes with porous silicas are disclosed in "Porous Silica," K. K. Unger, p. 108, Elsevier Scientific Publishing Co., NY, N.Y. (1979). A broad description of the reactions of silanes with a variety of materials is given in "Chemistry and Technology of Silicones," W. Noll, Academic Press, N.Y., N.Y. (1968).

The performance of a particular modified support material generally improves as the surface coverage of an asymmetric bidentate silane bonded to the surface of the support material increases. According to the present invention, subsequent to the reaction of a bidentate silane with the surface of a support structure, the surface of the support structure should be saturated.

As used herein, a "saturated" surface refers to a surface of a silica surface, subsequent to a reaction with an asymmetric bidentate silane, has substantially no nitrogen atoms bonded thereto as demonstrated by elemental analysis of the resulting modified support material.

It has been found that, during reaction of an asymmetric bidentate silane having dimethylamino groups with a silica substrate having silanol groups at its surface, rupture of the silicon-nitrogen bond readily occurs, allowing a high rate of reaction between the silane and the surface of the support structure. It has also been found that using these bidentate silanes results in comparatively high coverages of silane on the silica surface subsequent to the reaction of the silane with the silica surface.

The orientation of an asymmetric bidentate silane is bound to a silica surface can be characterized by $^{29}Si$ and $^{13}C$ cross-polarization magic-angle-spinning nuclear magnetic resonance spectroscopy (CP-MAS NMR) and diffuse reflectance infrared Fourier transform spectroscopy (DRIFT), as described in J. Chromatogr., 264, 197–213 (1983) and J. Chromatogr., 352, 275 (1986). The orientation and bonding characteristics of the various Si atoms has been assigned by $^{29}Si$ CP-MAS NMR. DRIFT spectroscopy can be used to identify the presence or absence of silanols at the surface of these modified support materials. The disappearance of a sharp peak at 3700 $cm^{-1}$ and the appearance of peaks in the 2800–3000 $cm^{-1}$ region of the spectra indicate the loss of isolated silanols and the formation of C—H structure due to bonding by the alkyl ligand.

The following examples are illustrative of certain embodiments of the present invention and are not to be construed as limiting. It is to be noted that, in the synthetic methods of the present invention, moisture sensitive materials were blanketed with dry nitrogen. All temperatures are reported in °C.

EXAMPLE 1

1-(octadecyl methyl dimethylaminosilyl)-2-(octyl methyldimethylaminosilyl) ethane:

$(Me_2N—SiMeC_{18}H_{37})—CH_2CH_2—(C_8H_{17}—SiMe—NMe_2)$ was prepared as follows. Dichloro-methylvinylsilane (92 grams, 0.8 moles, from the Aldrich Chemical Co., Milwaukee, Wis., USA) and 250 mL of tetrahydrofaran (THF) were added to a reaction flask. A 1M solution of octadecylmagnesium chloride (800 mL) in THF (from Aldrich Chemical Co.) was added portionwise over about 1.5 hours with stirring and cooling to 0° to 10°. The resulting dark mixture warmed to 26° during the next 30 minutes. Hexane was added (2 L), and the resulting solid was filtered off. The volatiles were removed from the filtrate on a rotary evaporator, and hexane was added to the residue. The solid was filtered off, and the volatiles removed from the filtrate again to yield an oil. Thionyl chloride (12 mL) was added to the oil to convert any silanol to chlorosilane. This solution was heated to 45° and allowed to stand overnight at ambient temperature. After removal of volatiles, the resulting black mixture was vacuum distilled, providing a 134-g fraction of octadecyl vinyl methylchlorosilane (compound A), as a clear, colorless oil with a boiling point of 170°–183°/0.1 mm. Gas chromatography/mass spectrometry (GC/MS) showed the product to be 87% octadecyl vinyl methylchlorosilane and 10% octadecyl chloride.

Dichloromethylsilane (184 mL, 1.77 moles, from Aldrich Chemical Co.) and 300 milliters of THF were added to a reaction flask. Octylmagnesium chloride (800 mL) was added at 0° to –10° over 2.5 h. The mixture was allowed to warm to ambient temperature, diluted with 2500 mL of hexane and filtered. Volatiles from this product were removed with a rotary evaporator. The residue was treated with hexane, and the solid was filtered off. The filtrate was evaporated to an oil. Vacuum distillation of the oil provided a fraction of 166 g of octyl methylchlorosilane (compound B), as a clear, colorless oil with a boiling point of 59°–62°/0.1 mm. GC/MS showed the product to be 97% octyl methylchlorosilane and 0.5% bis-(octyl methylsilyl) ether.

Compound B (61.3 g) and 0.05M $H_2PtCl_6$, 0.04 mole percent of a chloroplantinic acid/ethyl acetate solution was stirred and heated at 50° to 60° while the 134 g of compound A was added over 45 minutes. The mixture was kept at 60° C. for an additional hour to yield 1-(octadecyl methylchlorosilyl)-2-(octyl methylchlorosilyl) ethane (compound C), as a pale-yellow oil. The analysis calculated for this product $(C_{30}H_{64}Cl_2Si_2)$: C, 65.28; H, 11.69%. Elemental analysis showed: C, 65.80; H, 11.56%.

Compound C was added to a reaction flask fitted with a Dry-Ice consenser. Liquefied dimethylamine (82.2 mL) was dripped in during a one hour period with cooling to about 10°. A white solid was formed. The mixture was allowed to warm to 23° during the next hour, and this mixture was then diluted with 500 mL of hexane. The solid was filtered off and the filtrate concentrated to a clear, pale-yellow oil on a rotary evaporator. Vacuum distillation of the oil provided a fraction of 76.9 g of 1-(octadecyl methyl dimethylaminosilyl)-2-(octyl methyl dimethylaminosilyl)ethane (compound D), as a slightly colored oil with a boiling point of 230° to 258°/0.2 mm. The calculated analysis for this material $(C_{34}H_{76}N_2Si_2)$ is C, 71.75; H, 13.46; N, 4.92%. Elemental analysis showed: C, 72.41; H, 13.52; N, 4.32%.

EXAMPLE 2

1-(Methyl octadecyl dimethylaminosilyl)-2-(dimethyl dimethyl-aminosilyl) ethane:

$MeSi(NMe_2)C_{18}H_{37}—CH_2CH_2—Me_2SiNMe_2$ was prepared as follows. Chlorodimethylsilane (22.16 ML, 0.2 moles) and 1.5 mL of 0.05M $H_2PtCl_6$ in ethyl acetate were added to a reaction flask. Over a 40 minute period, 68.34 g (82% GC/MS assay, 0.156 moles) of compound A was added to the stirred mixture. The temperature increased from 22° to 56°. After an hour, the mixture solidified. Warm hexane (100 mL) was stirred in, and the resulting solution stripped of hexane on a rotary evaporator. This yielded a turbid yellow oil, which assayed (GC/MS) 96% 1-(methyl octadecylchlorosilyl)-2-(dimethylchlorosilyl)-ethane (compound E). This oil was vacuum distilled, with use of a 60° condenser water, providing forerun, then fraction #1 (boiling point 215°–220°/01 mm; 45.47 g; GC/MS assay: 95.4% compound E, 3.3% isomer, 1.3% unknown) and fraction #2 (boiling point 214°–210°/0.1 mm; 24.81 g; GC/MS assay: 98.6% compound E, 1.4% isomer). Fractions #1 and #2 were solids at room temperature.

Compound E (fraction #1, 45.13 g, 0.098 mole) was placed into a stirred reaction flask fitted with a Dry-Ice condenser. Liquefied dimethylamine (27.7 mL, 0.42 moles) of was added portionwise to the flask over a 45 minute period with the reaction flask temperature decreasing from 55° to 40°. After 30 minutes, the reaction mixture was cooled, diluted with 350 mL of hexane and stirred vigorously for 5 minutes. The mixture was filtered, and the filtrate stripped of volatiles on a rotary evaporator to yield a slightly colored oil. The oil was short-path vacuum distilled, providing a forerun, leaving a clear, colorless oil, boiling point 195°–206°, 31.69 g of 1-(methyl octadecyl dimethylaminosilyl)-2-(dimethyl dimethyl-aminosilyl) ethane (compound F). Calculated analysis for this compound was $(C_{27}H_{62}N_2Si_2)$ (formal weight 470.98): C, 68.86; H, 13.27; N, 5.95%. Elemental analysis showed: C, 68.36; H, 13.30; N, 4.5%.

EXAMPLE 3

1-(Methyl octadecyl dimethylaminosilyl)-2-(n-butyl methyl dimethylaminosilyl)ethane:

$MeSi(NMe_2)C_{18}H_{37}—CH_2CH_2—MeSiC_4H_9—NMe_2$ was prepared as follows. Methyldichlorosilane (193 grams, 1.68 moles) of and one liter of THF were added to a flask. This mixture was stirred and cooled to 5 ° to 10°. A 2 molar solution of n-butylmagnesium chloride (1.6 moles) in THF (Aldrich Chemical) was added over 3.25 hours, producing an exothermic reaction and white turbidity. The mixture was stirred overnight in a large water bath at ambient temperature, forming a relatively large amount of a white solid. The mixture was diluted with one liter of THF, filtered and the filtrate was concentrated on a rotary evaporator until it became thick with white solid. The solid was filtered off with the aid of hexane, and the filtrate evaporated on a rotary evaporator until precipitation of white solid. Filtration with hexane and concentration on the rotary evaporator gave a clear, yellow oil. The oil was distilled at atmospheric pressure, providing a fraction with a boiling point of 45° to 120° (97.04 g) and another fraction with a boiling point of 123° to 130° (75.96 g; by GC/MS: 88.5% butyl methylchlorosilane; 5.3% dibutyl methylsilane; 2.6% butyl methylsilanol). Redistillation of the latter fraction provided a fraction with a boiling point of 119° to 121° (52.7g) and GC/MS assay 92% butyl methylchlorosilane (compound G).

Compound G (52.0g, 0.35 mole at 92% assay), 3.1 mL of chloroplatinic acid solution (0.05M in ethyl acetate), then 25 mL of compound A (of a total of 143 g, 175 mL; 0.398 mole) were added to the reaction flask. The reaction mixture was heated to 50° to 55°, and the rest of compound A was added over 1.5 hour in this range, resulting in an exothermic reaction. After being held at 55° for an additional hour, the reaction mixture was short-path vacuum distilled, with a 60° condenser water, giving several fractions, one of which (76.6 g) exhibited a boiling point of 232° to 236°/0.05 mm. GC/MS of this product showed 98.0% [1-(octadecyl methyl chlorosilyl)-2-(butyl methyl chlorosilyl) ethane and isomer] (compound H).

Compound H (75.27 g) was added to a reaction flask fitted with a Dry-Ice condenser. The reaction flask was stirred and cooled to 10 while liquefied dimethylamine was added portionwise during 1 hour, forming a white solid. After 0.5 hours of additional vigorous stirring 350 mL of hexane was added, and this mixture was stirred an additional 45 minutes. The solid was filtered off and the filtrate stripped of volatiles on a rotary evaporator, leaving a residual oil. Short-path vacuum distillation of the oil gave a fraction (50.8 g) of clear, colorless oil, 1-(methyl octadecyl dimethylaminosilyl)-2-(n-butylmethyldimethylaminosilyl)-ethane (compound I), with a boiling point of 230° to 232°/0.05 mm. Calculated analysis for this product($C_{30}H_{68}N_2Si_2$)(formula weight 513.06) was C, 70.23; H, 13.36; N, 5.46%. Elemental analysis showed: C, 70.12; H, 13.32; N, 5.02%.

EXAMPLE 4

The following is a prophetic example of the synthesis of 1-(octadecyl methyl dimethylaminosilyl)-3-{methyl[4-(chlorosulfonyl)phenethyl] dimethylaminosilyl} propane MeSi(NMe$_2$)Cl$_8$H$_{37}$—CH$_2$CH$_2$CH$_2$—MeSi[4—(ClO$_2$S)—Ph CH$_2$CH$_2$]NMe$_2$ Phenethylmethyldichlorosilane (Gelest, Inc., Tullytown, Pa., USA) is chlorosulfonated with chlorosulfonic acid as described in Chem. Abstr. 103 P71494v. This yields [4-(chlorosulfonyl)phenethyl] methyldichlorosilane which is reacted with allyl-magnesium chloride to form [4-(chlorosulfonyl)phenethyl] methyl allylchlorosilane. This product is reacted with octadecyl methylchlorosilane (boiling point of 175° to 177°/0.5 mm, from reaction of octadecylmagnesium bromide with methyldichlorosilane) under chloroplatinic acid catalysis to form 1-(octadecyl methylchlorosilyl)-3-{methyl [4-(chlorosulfonyl)phenethyl] chlorosilyl}propane. This material is reacted with dimethylamine to form 1-(octadecyl methyl dimethylaminosilyl)-3-{methyl [4-(chlorosulfonyl)-phenethyl] dimethylaminosilyl}propane.

This silane reagent is reacted with surface-reactive silica (general procedure described below), followed by mild aqueous hydrolysis to produce a bonded-phase composition with propane, 1-(octadecyl methylsilyl)-3-[(4-sulfophenethyl) methylsilyl] bonded to silica.

PSiO—SiMeC$_{18}$H$_{37}$—CH$_2$CH$_2$CH$_2$—MeSi[4—(HO$_3$S)—PhCH$_2$CH$_2$]—OSiP

EXAMPLE 5

PSiO-SiMeC$_{18}$H$_{37}$—CH$_2$CH$_2$—Me$_2$Si—OSiP was prepared as follows.

Silica (25.0 g, 5-μm Zorbax Rx-SIL, 174 m$^2$/g; Hewlett-Packard Co., Wilmington, Del.) and 250 mL of toluene were added to a reaction flask. The stirred mixture was boiled under reflux with azeotropic removal of water along with 100 mL of toluene, and cooled below reflux. 75 mL of toluene and 7.66 g (0.0375 mole) compound F were added. The moisture trap was replaced with a dry reflux condenser, and the stirred mixture was boiled under reflux for 18 h. The hot mixture was filtered, and the solid was washed with 300 mL of hot toluene, 150 mL of THF and 150 mL of acetonitrile. This mixture was sucked "dry" on the filter, and further dried in a vacuum oven (110°, air sweep, 20" Hg vacuum, 45 min). Elemental analysis showed: C, 8.92; H, 1.74; N, 0.00%.

The silica derivative can have residual unreacted silanol groups reacted ("endcapped") with, for example, N, N'-dimethyltrimethylsilyamine or hexamethyldisilazane, or it can be double-endcapped with dimethylsilyl and trimethylsilyl groups. The above solid was double endcapped by dimethylsilylation and trimethylsilylation [J. Chromatogr. A762, 97 (1997)]. Elemental analysis for this end-capped, bonded-phase composition was: C, 9.08; H, 1.74; N, 0.00%.

EXAMPLE 6

PSiO—SiMeC$_{18}$H$_{37}$—CH$_2$CH$_2$—MeSiC$_4$H$_9$—OSiP was prepared as follows.

Silica (25.0 g 5-μm Zorbax Rx-SIL, 174 m$^2$/g; Hewlett-Packard Co., Wilmington, Del.) and 250 mL of toluene were added to a reaction flask. The stirred mixture was boiled under reflux with azeotropic removal of moisture and 114 mL of toluene and cooled below reflux. The moisture trap was replaced with a dry reflux condenser, and 18.6 g of compound I were added. The stirred mixture was boiled under reflux for 19 hours. The hot mixture was filtered and washed with hot: toluene (300 mL), THF (150 mL), and acetonitrile (150 mL). This mixture was sucked "dry" on the filter, and further dried in a vacuum oven (110 °, air sweep, 20" Hg vacuum, 45 min). Elemental analysis showed: C, 8.96; H, 1.77; N, 0.00%.

The solid was endcapped by dimethylsilylation and trimethylsilylation [J. Chromatogr. A762, 97 (1997)]. Analysis found for this further-capped, bonded-phase composition: C, 9.12; H, 1.80%.

EXAMPLE 7

PSiO-SiMeC$_{18}$H$_{37}$—CH$_2$CH$_2$—MeSiC$_4$H$_9$—OSiP was prepared as follows.

Silica (25.0 g 5-μm Zorbax Rx-SIL, 183 m$^2$/g; Hewlett-Packard Co., Wilmington, Del.) and 250 mL of toluene were added to a reaction flask. The stirred mixture was boiled under reflux with removal of moisture and 45 mL of toluene. The moisture trap was replaced with a dry reflux condenser, and 19 g of compound I was added. The stirred mixture was boiled under reflux for 71 hours. The mixture was filtered hot and washed with 150 mL each of hot: toluene, THF, and acetonitrile. This mixture was sucked "dry" on the filter, and dried in a vacuum over (110°, air sweep, 20" Hg vacuum, 45 min). Elemental analysis showed: C, 9.12; H, 1.80; N, 0.00%.

The solid was endcapped by dimethylsilylation and trimethylsilylation [J. Chromatogr. A762, 97 (1997)]. Analysis found for this endcapped, bonded-phase composition: C, 9.32: H, 1.71; N, 0.00%.

EXAMPLE 8

PSiO-SiMeC18H$_{37}$—CH$_2$CH$_2$—MeSiC$_8$H$_{17}$—OSiP was prepared as follows.

Silica (35.0 g Zorbax Rx-SIL; 80 Å, 183 m$^2$/g; Hewlett Packard Co., Wilmington, Del.) and 300 mL of toluene were added to a reaction flask. The stirred mixture was boiled under reflux with azeotropic removal of moisture and 56 mL of toluene. The moisture trap was replaced with a dry reflux condenser, and the mixture was cooled below reflux. Compound D (29.84 g) was added, and the stirred mixture was boiled under reflux for 72 hours. The mixture was filtered hot and washed with hot: toluene, THF, and acetonitrile, and sucked "dry" on the filter. A sample was dried in a vacuum oven at 110 with air sweep, at 20" Hg vacuum for 2 h. For this dried, bonded-phase composition, elemental analysis showed: C, 10.16; H, 1.86%.

The silica derivative was dimethylsilylated and trimethylsilylated [J. Chromatogr. A762, 97 (1997)]. Elemental analysis or this dried, further-capped, bonded-phase composition showed: C, 10.50; H, 1.94%.

EXAMPLE 9

FIG. 1 shows the amount of silica dissolved as double-endcapped (J. Chromatogr. A762, 97 (1997)) bonded-phase packings (support materials). The surfaces of these support materials were modified with dimethyl($C_8H_{17}$)Si (dimethyl-C8), dimethyl($C_{18}H_{37}$)Si (dimethyl-C18), dimethyl-Si-$(CH_2)_2$-Si-methyl($C_{18}H_{37}$) (C1/C18 Bidentate) or methyl($C_8H_{17}$)—Si—$(CH_2)_2$—Si—methyl($C_{18}H_{37}$) (C8/C18 Bidentate). Prior to surface modification, the silica support materials were similar for each type of silane. The columns were continuously purged with a mobile phase solution of 50% acetonitrile/50% 0.02 molar potassium phosphate buffer at pH 11. The flow rate was 1.5 mL/minute, and the temperature was 25. The concentration of the silicate formed in the column effluent was measured calorimetrically using the silicomolybdate method disclosed in J. Chromatogr. A728, 259 (1996).

As clearly demonstrated in FIG. 1, the rate of silica support degradation (dissolution) was significantly lower for supports modified with the asymmetric bidentate silanes of the present invention relative to conventional monofunctional (one silicon atom) silanes. This result indicates that use of the bidentate silanes of the present invention result in more stable modified support materials.

EXAMPLE 10

Figure 2:
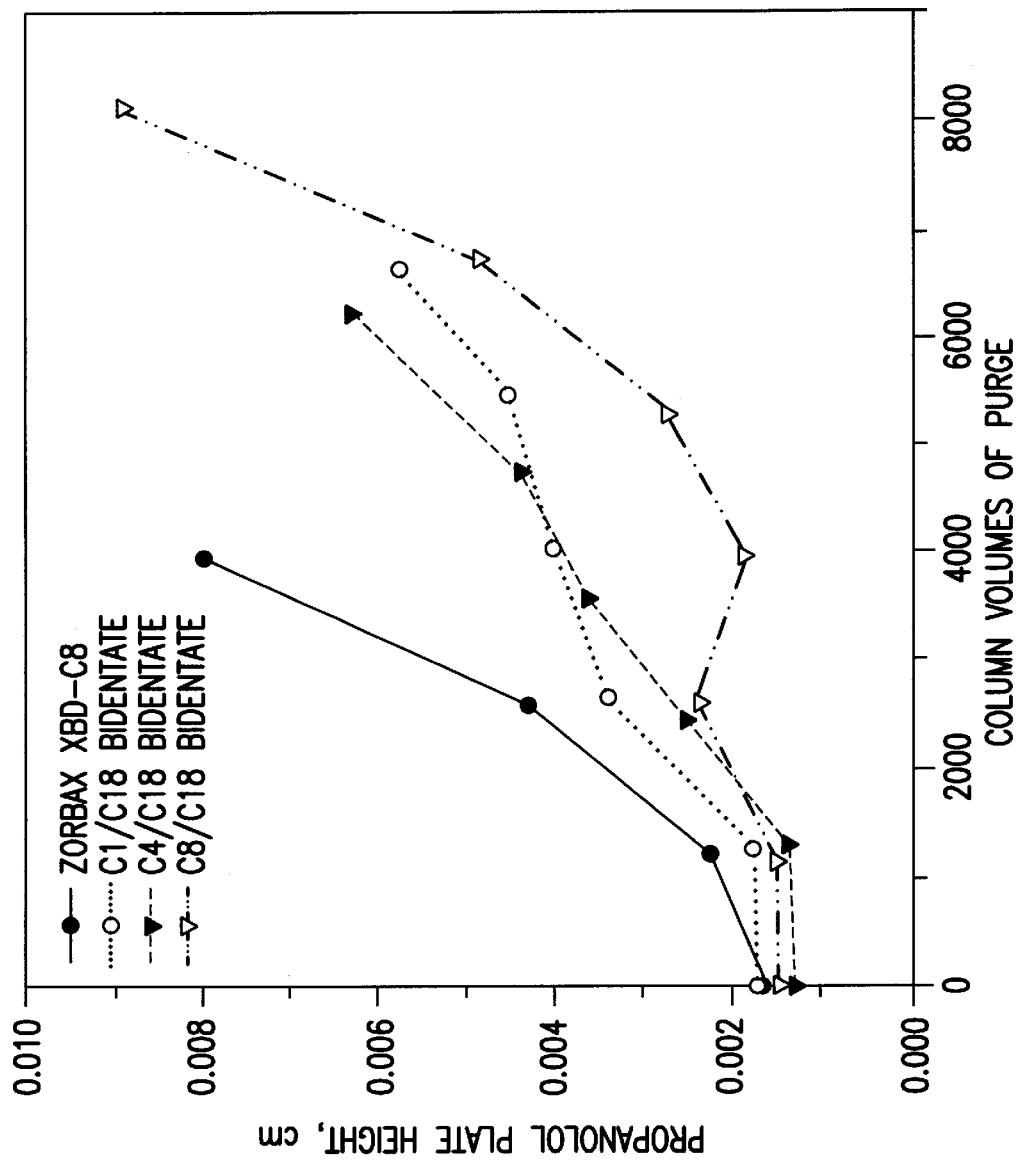
FIG. 2 is a graph comparing the propanolol plate height of modified support materials according to two embodiments of the present invention with that modified support materials according to the related art.
Figure 3A:
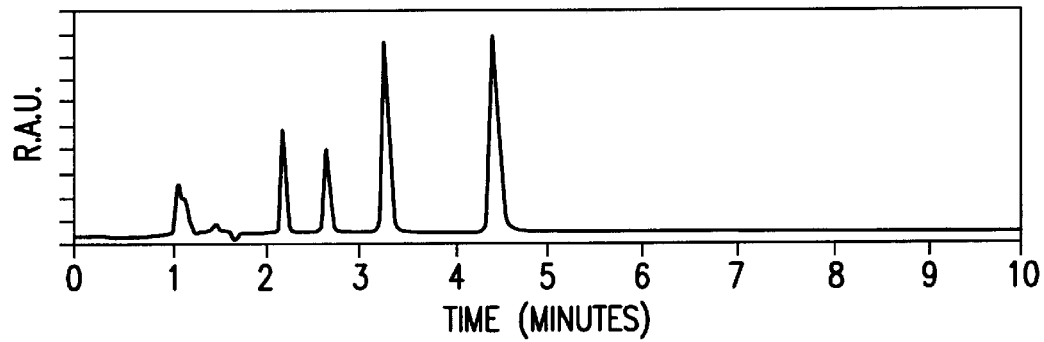
FIGS. 3A, 3B, 3C and 3D are chromatographs of separations with an aggressive mobile phase according to one embodiment of the present invention and the related art before and after a large number of a large number of column volumes.
Figure 3B:
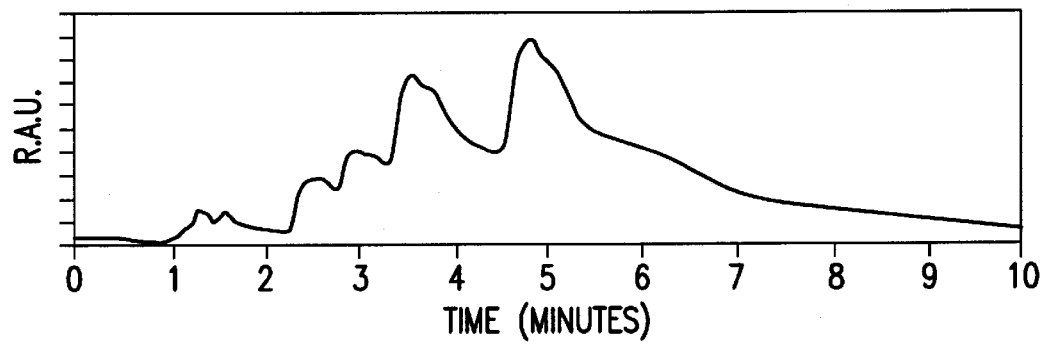
Figure 3C:
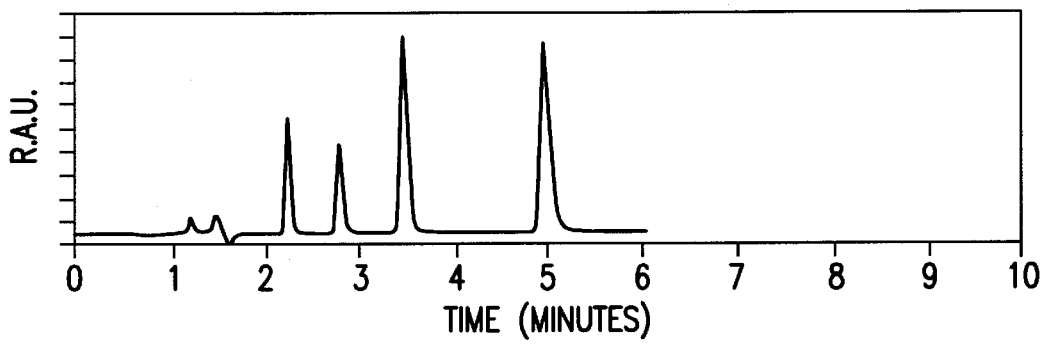
Figure 3D:
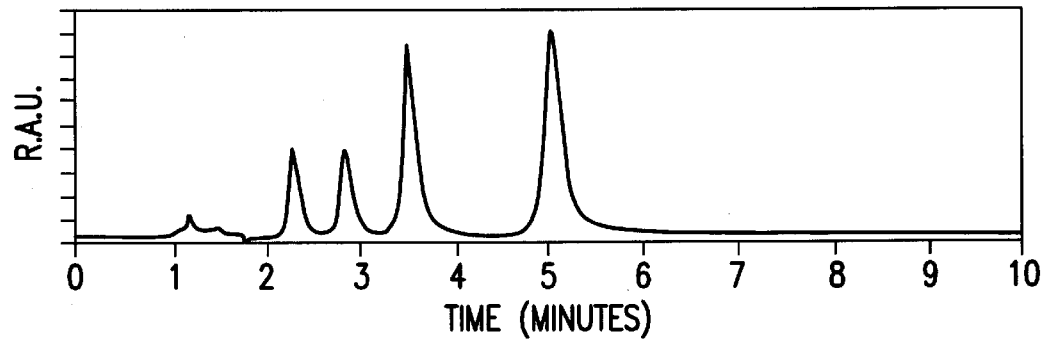

FIG. 2 shows the column plate height measured for chromatographic columns formed from silica supports modified with dimethyl($C_8H_{17}$)Si (Zorbax XDB-C8), methyl($C_4H_9$)—Si—$(CH_2)_2$-Si-methyl($C_{18}H_{37}$) ($C_4/C_{18}$ Bidentate), dimethyl-Si-$(CH_2)_2$-Si-methyl($C_{18}H_{37}$)($C_1/C_{18}$ Bidentate) or methyl($C_8H_{17}$)-Si-$(CH_2)_2$-Si-methyl($Cl_8H_{37}$) ($C_8/C_{18}$ Bidentate). These higher plate heights achieved using the asymmetric bidentate silanes of the present invention clearly demonstrate the improved stability of the modified support materials created using these silanes relative to conventional monofunctional silanes. It is to be noted that silica supports modified with methyl($C_8H_{17}$)-Si-$(CH_2)_2$-Si-methyl($C_{18}H_{37}$) ($C_8/C_{18}$ Bidentate) showed the highest plate number (stability). This enhanced stability is believed to result from the bulkier nature of this asymmetric silane.

EXAMPLE 11

FIGS. 3A through 3D show chromatographs, in terms of relative absorption units (R.A.U.) as a function of retention time, for chromatographic columns with silica supports modified with dimethyl($C_8H_{17}$)Si (Zorbax XD8-C8) or dimethyl-Si-$(CH_2)_2$-Si-methyl($Cl_8H_{37}$) ($C_1/C_{18}$ Bidentate). The chromatographs for each column were taken before and after these columns were flushed with 6,626 (monofunctional silane) or 6,664 (asymmetric bidentate silane) column volumes of a pH 11 mobile phase. The ability of the silica support structure modified with the conventional monofunctional silane to separate the species in the mobile phase is greatly reduced. In contrast, the ability of the silica support structure modified with the conventional monofunctional silane to separate the species in the mobile phase is largely unchanged.

EXAMPLE 12

Figure 4:
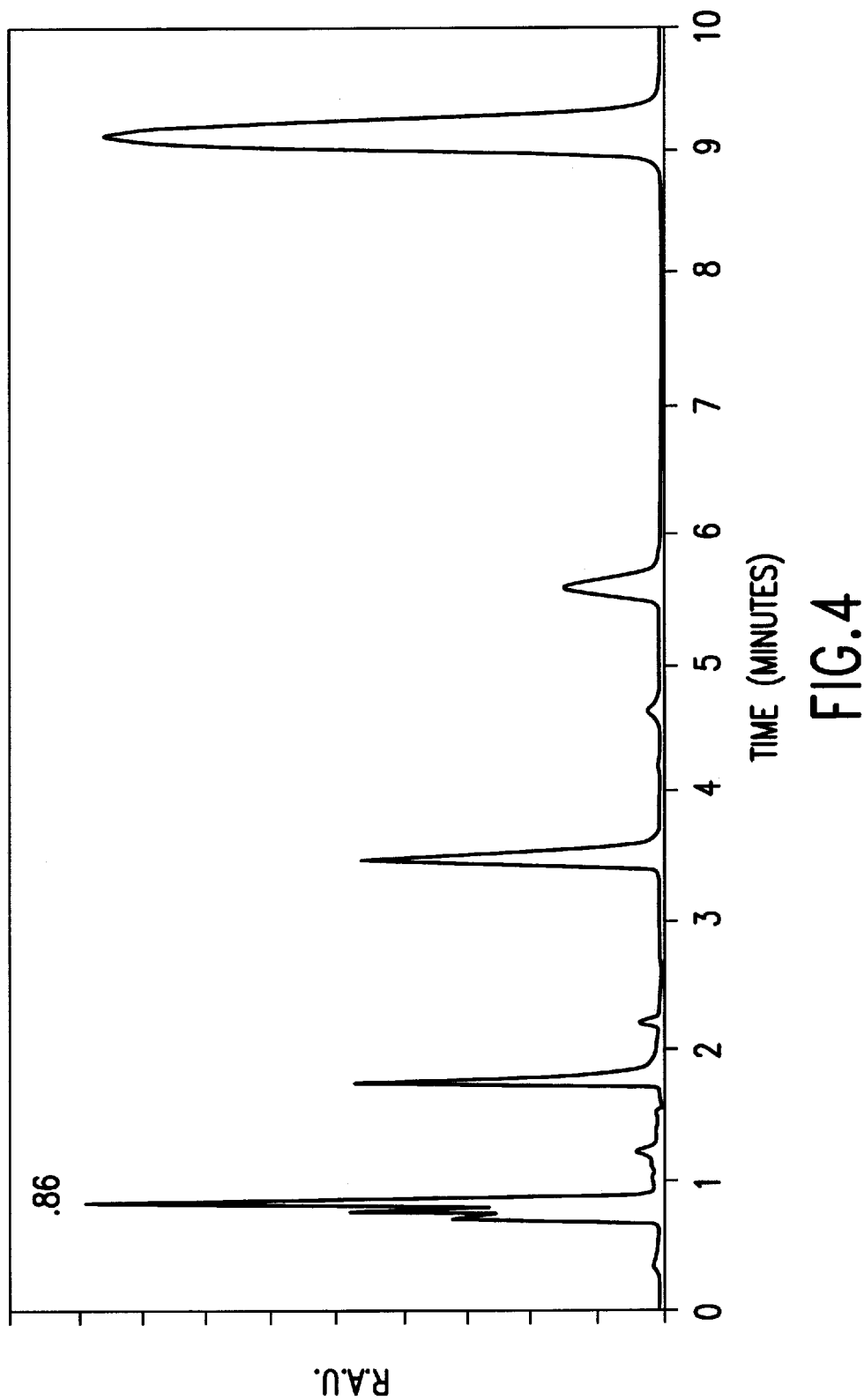
FIG. 4 is a chromatograph of a separation of a carrier phase using a modified support material according to one embodiment of the present invention.

FIG. 4 shows a chromatograph, in terms of R.A.U. as a function of retention time, for a silica support modified with methyl($C_8H_{17}$)-Si-$(CH_2)_2$-Si-methyl($C_{18}H_{37}$) ($C_8/C_{18}$ Bidentate). The mobile phase included a mixture of basic drugs, and the pH of the mobile phase was 7. This is a challenging solution to separate since the species in the mobile phase and any unreacted silanol groups at the silica surface are partially ionized, creating an environment conducive to undesirable ion-exchange effects (as opposed to the desired hydrophobic interaction effect). Using a silica support modified with a conventional art silane can result in low column efficiency and poorly resolved and/or asymmetric peak heights. The superior kinetic characteristics demonstrated by this chromatograph (i.e., high column efficiency and sharply resolved and symmetric peak shapes) is believed to result from both the increased stability of the asymmetric bidentate silanes of the present invention and the unique ability of such silanes to space the larger hydrocarbon R groups in a manner that results in improved chromatographic performance.

Additional comparative results are shown in Table 1.

TABLE 1

| Phase | Reaction time, hrs. | % $C^a$ | Amitriptyline[b] | | |
|---|---|---|---|---|---|
| | | | N | k | As |
| Zorbax XDB-C8 | 24 | 7.15 | 9002 | 3.77 | 1.53 |
| Zorbax XDB-C18 | 72 | 9.38 | 9055 | 6.44 | 1.47 |
| C1/C18 bidentate | 18 | 9.08 | 8802 | 6.02 | 1.84 |
| C4/C18 bidentate | 21 | 9.13 | 9607 | 5.86 | 1.49 |
| C4/C18 bidentate | 72 | 9.32 | 9923 | 5.98 | 1.39 |
| C8/C18 bidentate | 18 | 10.50 | 10035 | 5.55 | 1.27 |
| C18/C18 bidentate | 71 | 12.09 | 5990 | 5.22 | 2.07 |
| C18/C18[c] bidentate | 72 | 12.09 | 4413 | 5.25 | 3.37 |
| C18/C18P bidentate | 71 | 11.94 | 9377 | 5.31 | 1.57 |

P = propylene bridge
[a] After double endcapping
[b] 60% ACN/40% 0.01M Na phosphate buffer, pH 7.0, 1.0 mL/min, 40° C.
[c] Reaction in p-cymene at 165° C.

In Table I, "N" represents the plate height of a column, "k" is a normalized retention value of a column, and "As" is the peak assymetry value in the corresponding chromatograph. These terms are known to those skilled in the art and are described in, for example, "An Introduction to Modem Liquid Chromatography," L. R. Snyder and J. J. Kirkland, Second Edition, John Wiley, N.Y., N.Y. (1979).

As demonstrated in Table 1, the asymmetric bidentate silanes of the present invention result in modified support structures with no substantial reduction in column efficiency relative to monofunctional silanes or symmetric bidentate silanes. In particular, the superior asymmetry peak features (As closer to one) for the asymmetric bidentate silanes indicates that the support materials modified with these silanes have a high silane coverage relative to supports modified with monofunctional silanes or symmetric bidentate silanes. This reduces the potential for disadvantageous interactions between species in the mobile phase and the support material, increasing the symmetry values for peaks corresponding to species that are separated later in time during a chromatographic procedure. It is to be noted that increasing the reaction time from 19 hours to 71 hours resulted in little change in the chromatographic values for methyl($C_4H_9$)—Si—$(CH_2)_2$-Si-methyl($C_{18}H_{37}$). This demonstrates that, at 19 hours, the silane was nearly fully reacted with both ends of the silane believed to be covalently attached to the surface of the silica support.

Having thus described certain embodiments of the present invention, various alterations, modifications and improvements will be apparent to those skilled in the art. Such alterations, modifications and improvements are intended to be within the spirit and scope of the present invention. Accordingly, the foregoing description is by way of example only and not to be construed as limiting. The present invention is limited only as described by the following claims and the equivalents thereto.

What is claimed is:

1. A support composition having a structure:

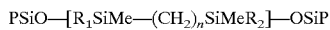

PSiO—[R$_1$SiMe—(CH$_2$)$_n$SiMeR$_2$]—OSiP wherein n–2 or 3, R$_1$ is an alkyl group having from 1 to 30 carbon atoms, R$_2$ is an alkyl group having from 8 to 18 carbon atoms, Me is a methyl group and PSiO is a surface-reacted silica, and wherein R$_1$ is a different alkyl group than R$_2$.

2. The support composition according to claim 1, wherein the support composition is end capped.

3. The support composition according to claim 2, wherein R$_1$ is a hydrocarbon group having from 8 to 30 carbon atoms.

4. The support composition according to claim 3, wherein R$_2$ includes a functional group selected from the group consisting of —(CH$_2$)$_3$—N$^+$Cl$^-$, —(CH$_2$)$_2$—C$_6$H$_4$—SO$_3$H, —(CH$_2$)$_3$—C$_6$H$_4$—SO$_3$H, —(CH$_2$)$_3$—O—CH$_2$—CHOH—CH$_2$OH, —(CH$_2$)$_3$—NH$_2$ and —(CH$_2$)$_3$—CN.

5. The support composition according to claim 1, wherein R$_2$ includes a functional group selected from the group consisting of —(CH$_2$)$_3$—N$^+$Cl$^-$, —(CH$_2$)$_2$—C$_6$H$_4$—$_{SO3}$H, —(CH$_2$)$_3$—O—CH$_2$—CHOH—CH$_2$OH, —(CH$_2$)$_3$—NH$_2$ and —(CH$_2$)$_3$—CN.

6. The support composition according to claim 1, wherein R$_1$ is a hydrocarbon group having from 8 to 30 carbon atoms.

7. The composition according to claim 1, wherein R$_1$ is an n-butyl group and R$_2$ is an n-octadecyl group.

8. The support composition according to claim 1, wherein R$_1$ is an n-octyl group and R$_2$ is an n-octadecyl group.

9. The support composition according to claim 1, wherein R$_1$ is a methyl group and R$_2$ is an n-octadecyl group.

10. The support composition according to claim 2, wherein R$_1$ is an n-butyl group, n has a value of 2 and R$_2$ is an n-octadecyl group.

11. The support composition according to claim 2, wherein R$_1$ is an n-octyl group, n has a value of 2 and R$_2$ is an n-octadecyl group.

12. A bidentate silane having a molecular formula:

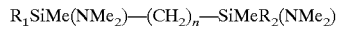

R$_1$SiMe(NMe$_2$)—(CH$_2$)$_n$—SiMeR$_2$(NMe$_2$)

wherein R$_1$ is an alkyl group having from 1 to 30 carbon atoms, R$_2$ is an alkyl group having from 8 to 18 carbon atoms, Me is a methyl group and n has a value of 2 or 3, and wherein R$_1$ is a different alkyl group than R$_2$, wherein R$_2$ includes a functional group selected from the group consisting of —(CH$_2$)$_3$—N$^+$Cl$^-$, —(CH$_2$)$_2$—C$_6$H$_4$—(CH$_2$)$_3$—C$_6$H$_4$—SO$_3$H, —(CH$_2$)$_3$—O—CH$_2$—CHOH—CH$_2$ OH, —CH$_2$)$_3$—NH$_2$ and —(CH$_2$)$_3$—CN.

* * * * *